US009416068B2

(12) United States Patent
Corma Canos et al.

(10) Patent No.: US 9,416,068 B2
(45) Date of Patent: Aug. 16, 2016

(54) METHOD FOR CONVERTING BIOMASS INTO LIQUID FUEL

(71) Applicants: CONSEJO SUPERIOR DE INVESTIGACIONES CIENTIFICAS (CSIC), Madrid (ES); UNIVERSIDAD POLITECNICA DE VALENCIA, Valencia (ES)

(72) Inventors: Avelino Corma Canos, Valencia (ES); Michael Renz, Valencia (ES); Olalla De La Torre Alfaro, Valencia (ES)

(73) Assignees: CONSEJO SUPERIOR DE INVESTIGACIONES CIENTIFICAS (CSIC), Madrid (ES); UNIVERSIDAD POLITECNICA DE VALENCIA, Valencia (ES)

( * ) Notice: Subject to any disclaimer, the term of this patent is extended or adjusted under 35 U.S.C. 154(b) by 418 days.

(21) Appl. No.: 13/714,542

(22) Filed: Dec. 14, 2012

(65) Prior Publication Data
US 2013/0158315 A1 Jun. 20, 2013

Related U.S. Application Data

(63) Continuation of application No. PCT/ES2011/070372, filed on May 23, 2011.

(30) Foreign Application Priority Data

Jun. 16, 2010 (ES) .................................. 201030928

(51) Int. Cl.

| C07C 1/20 | (2006.01) |
|---|---|
| C07C 2/02 | (2006.01) |
| C07C 2/04 | (2006.01) |
| C07C 5/02 | (2006.01) |
| C07C 5/27 | (2006.01) |
| C07C 1/24 | (2006.01) |
| C10G 3/00 | (2006.01) |
| C10G 45/10 | (2006.01) |
| C10G 50/00 | (2006.01) |
| C10G 69/12 | (2006.01) |
| C10G 45/02 | (2006.01) |
| B01J 21/18 | (2006.01) |
| B01J 23/36 | (2006.01) |
| B01J 23/40 | (2006.01) |
| B01J 23/42 | (2006.01) |
| B01J 23/72 | (2006.01) |
| B01J 23/755 | (2006.01) |
| B01J 27/02 | (2006.01) |

(52) U.S. Cl.
CPC ... *C07C 1/24* (2013.01); *C10G 3/44* (2013.01); *C10G 3/45* (2013.01); *C10G 3/47* (2013.01); *C10G 3/48* (2013.01); *C10G 3/52* (2013.01); *C10G 45/02* (2013.01); *C10G 45/10* (2013.01); *C10G 50/00* (2013.01); *C10G 69/126* (2013.01); *B01J 21/18* (2013.01); *B01J 23/36* (2013.01); *B01J 23/40* (2013.01); *B01J 23/42* (2013.01); *B01J 23/72* (2013.01); *B01J 23/755* (2013.01); *B01J 27/02* (2013.01); *C10G 2300/1011* (2013.01); *C10G 2300/1014* (2013.01); *C10G 2400/04* (2013.01); *Y02P 30/20* (2015.11)

(58) Field of Classification Search
CPC .............. C07C 1/20; C07C 2/00; C07C 2/02; C07C 2/04; C07C 2/06; C07C 2/08; C07C 2/14; C07C 2/16; C07C 2/42; C07C 5/00; C07C 5/02; C07C 5/03; C07C 5/27; C07C 5/2702; C07C 5/2729
USPC .................................. 585/240, 250, 254, 255
See application file for complete search history.

(56) References Cited

U.S. PATENT DOCUMENTS

| 3,287,374 | A | * | 11/1966 | Dunlop et al. ................. 549/473 |
|---|---|---|---|---|
| 7,880,049 | B2 | | 2/2011 | Dumesic et al. |
| 2007/0161832 | A1 | * | 7/2007 | Myllyoja et al. .................. 585/7 |
| 2009/0124839 | A1 | * | 5/2009 | Dumesic et al. .............. 585/251 |
| 2010/0317823 | A1 | * | 12/2010 | Boussie et al. ................. 528/323 |

FOREIGN PATENT DOCUMENTS

| WO | 2008/109877 | 9/2008 |
|---|---|---|
| WO | 2008/151178 | 12/2008 |
| WO | 2009/030510 | 3/2009 |

OTHER PUBLICATIONS

International Search Report issued Oct. 25, 2011 in International (PCT) Application No. PCT/ES2011/070372.
J. Chheda et al., "An overview of dehydration, aldol-condensation and hydrogenation processes for production of liquid alkanes from biomass-derived carbohydrates", Catalysis Today, vol. 123, pp. 59-70, 2007.

(Continued)

*Primary Examiner* — In Suk Bullock
*Assistant Examiner* — Philip Louie
(74) *Attorney, Agent, or Firm* — Wenderoth, Lind & Ponack, L.L.P.

(57) ABSTRACT

The invention relates to a method for producing liquid fuel having a high alkane content and a low oxygenized compound content, said method comprising at least: a first step of treating 2-methylfuran with a catalyst and water in reaction conditions in order to form a mixture of products with at least ten carbon atoms; and a second step of catalytic hydrogenation and dehydration of the product or the mixture obtained in step 1, using suitable hydrogenation and dehydration catalysts.

19 Claims, 1 Drawing Sheet

(56) References Cited

OTHER PUBLICATIONS

P. Blommel et al., "Catalytic conversion of sugar into conventional gasoline, diesel, jet fuel, and other hydrocarbons", International Sugar Journal, vol. 110, pp. 672-679, 2008.

I. Iovel et al., "Hydroxymethylation and alkylation of compounds of the furan, thiophene, and pyrrole series in the presence of $H^+$ cations (review)", Chemistry of Heterocyclic Compounds, vol. 34, No. 1, pp. 1-12, 1998.

H. Zheng et al., "Towards understanding the reaction pathway in vapour phase hydrogenation of furfural to 2-methylfuran", Journal of Molecular Catalysis A: Chemical, vol. 246, pp. 18-23, 2006.

A. Corma et al., "Production of High-quality Diesel from Biomass Waste Products". Angew. Chem. Int. Ed., vol. 50, pp. 2375-2378, 2011.

Tao et al., "MCM-41 supported Mo/Zr mixed oxides as catalysts in liquid phase condensation of 2-methylfuran with acetone", Journal of Molecular Catalysts A: Chemical, vol. 198, 2003, pp. 139-149.

Dumesic et al., "Liquid-Phase Catalytic Processing of Biomass-Derived Oxygenated Hydrocarbons to Fuels and Chemicals", Angew. Chem. Int. Ed., vol. 46, Jul. 2007, pp. 7164-7183.

Barret et al., "Single-reactor process for sequential aldol-condensation and hydrogenation of biomass-derived compounds in water", Applied Catalysis B: Environmental, vol. 66, Apr. 2006, pp. 111-118.

Huber et al., "Production of Liquid Alkanes by Aqueous-Phase Processing of Biomass-Derived Carbohydrates", Science, vol. 308, Jun. 2005, pp. 1446-1450.

Bond et al., "Integrated Catalytic Conversion of $\gamma$-Valerolactone to Liquid Alkenes for Transportation Fuels", Science, vol. 327, Feb. 2010, pp. 1110-1114.

Leshkov et al., "Production of dimethylfuran for liquid fuels from biomass-derived carbohydrates", Nature Publishing Group, vol. 447, Jun. 2007, pp. 982-986.

Huber et al., "Renewable Alkanes by Aqueous-Phase Reforming of Biomass-Derived Oxygenates", Angew. Chem. Int. Ed., vol. 43, 2004, pp. 1549-1551.

Gonzalez et al., "Polymerization of furfuryl alcohol with trifluoroacetic acid, $2^{a)}$, The formation of difurfuryl ether", Makromol. chem., Rapid Commun., vol. 13, 1992, pp. 517-523.

Zeitsch, "The chemistry and technology of furfural and its many by-products", sugar series, vol. 13, 2000, p. 229-230.

Schniepp et al., "The Preparation of Acetopropyl Alcohol and 1,4-Pentanediol from Methylfuran", J. Am. Chem. Soc., vol. 69, Mar. 1947, pp. 672-674.

\* cited by examiner

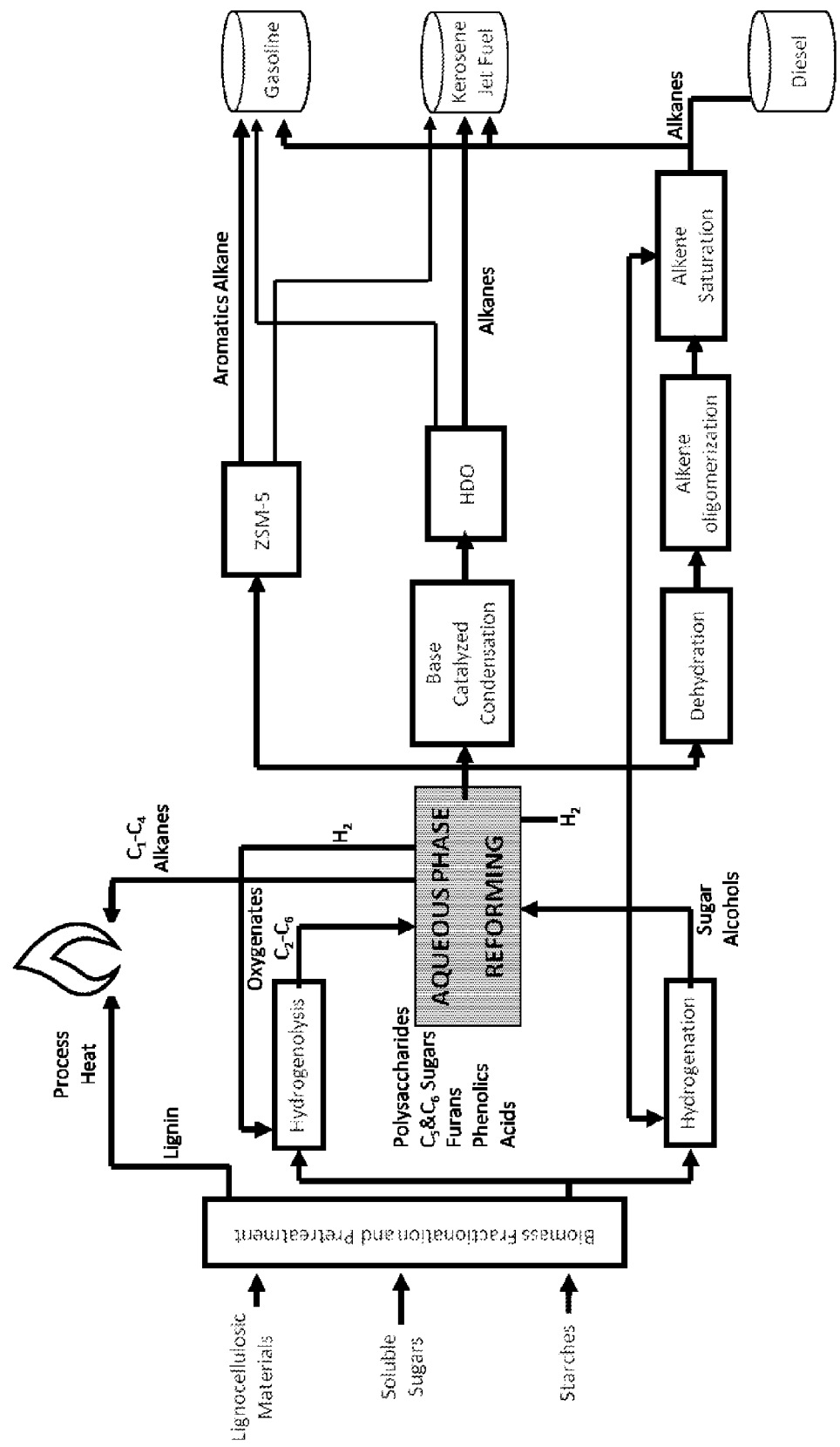

METHOD FOR CONVERTING BIOMASS INTO LIQUID FUEL

FIELD OF THE INVENTION

This invention belongs to the field of the conversion of plant biomass into fuels for transport.

STATE OF THE ART PRIOR TO THE INVENTION

Biofuels are plant origin fuels, which have characteristics similar to those of fossil fuels, allowing their use in barely modified engines. These fuels have several environmental advantages. In the case that the biofuels are from plant origin, the balance of carbon dioxide in their combustion is theoretically neutral since it can be considered that that same amount of carbon dioxide produced in said combustion, has been previously consumed from the carbon dioxide of the atmosphere through the photosynthesis cycles (over a period of years). In addition, biofuels do not contain or contain low amounts of nitrogen and sulfur compounds. Therefore, their combustion will not produce, or if it does it should be in smaller amounts than in the case of fossil fuels, nitrogen and sulfur oxides that cause irritation and damage to the respiratory system and which are the source of tropospheric ozone formation and smog. It is known that these oxides promote the formation of acid rain, the sulphur oxides being the main cause of the same.

The first generation of biofuels was primarily focused on biodiesel (together with bioethanol). Nowadays, the fatty acid methyl and ethyl esters are called biodiesel (or FAMEs). Biodiesel is obtained by transesterification of vegetable oils with methanol or ethanol. This biofuel has some disadvantages that limit its use in current engines in amounts of the order of 6%. Another drawback of biodiesel is that an extended or inappropriate storage may favor its decomposition and the release of fatty acids. These acids are not completely soluble in the mix and the formation of solids can cause problems in ducts and filters, in addition to the possible corrosion caused by their acid properties. However, the main reason why the biodiesel cannot currently replace the conventional diesel is related to the fact that the vegetable oil is obtained mainly from crop plants which makes it compete for cropland. This means that in the end the production of biodiesel competes with food production, significantly increasing the price of some basic foods.

To avoid the competition with food production a second generation of biofuels has been developed, which must avoid plants, seeds, tubers, etc. that have direct use as food and, in general, any plant biomass that requires cropland. On these bases it is intended to develop second generation biofuels from hemicellulose or cellulose that can be derived from wood (chips or sawdust) but also any kind of vegetable biomass residue.

Possible solutions to the problem of the production of second-generation biofuels have been recently suggested. In the method described by J. A. Dumesic and col. (*Science* 2005, 308, 1446-1450; PTC Int. Appl. WO2008151178, 2008; US Patent 20090124839, 2007) is carried out the aldol condensation of 5-hydroxymethylfurfural (HMF; or of furfural) to obtain molecules with 9, 12 or 15 carbon atoms (see scheme 1) that in subsequent steps can be hydrogenated to their corresponding alkanes. This technology has several drawbacks. For example the fact that the aldol condensation needs a second raw material since an aldol condensation of the HMF or the furfural with itself is not possible, so it is necessary to carry out a crossed aldol condensation. With this purpose, Dumesic and collaborators use acetone as connector of two furanic molecules. However, a crossed aldol condensation involves, by its nature, lower selectivity, since the acetone can condense with itself.

Scheme 1 (adapted from *Science* 2005, 308, 1446-1450).

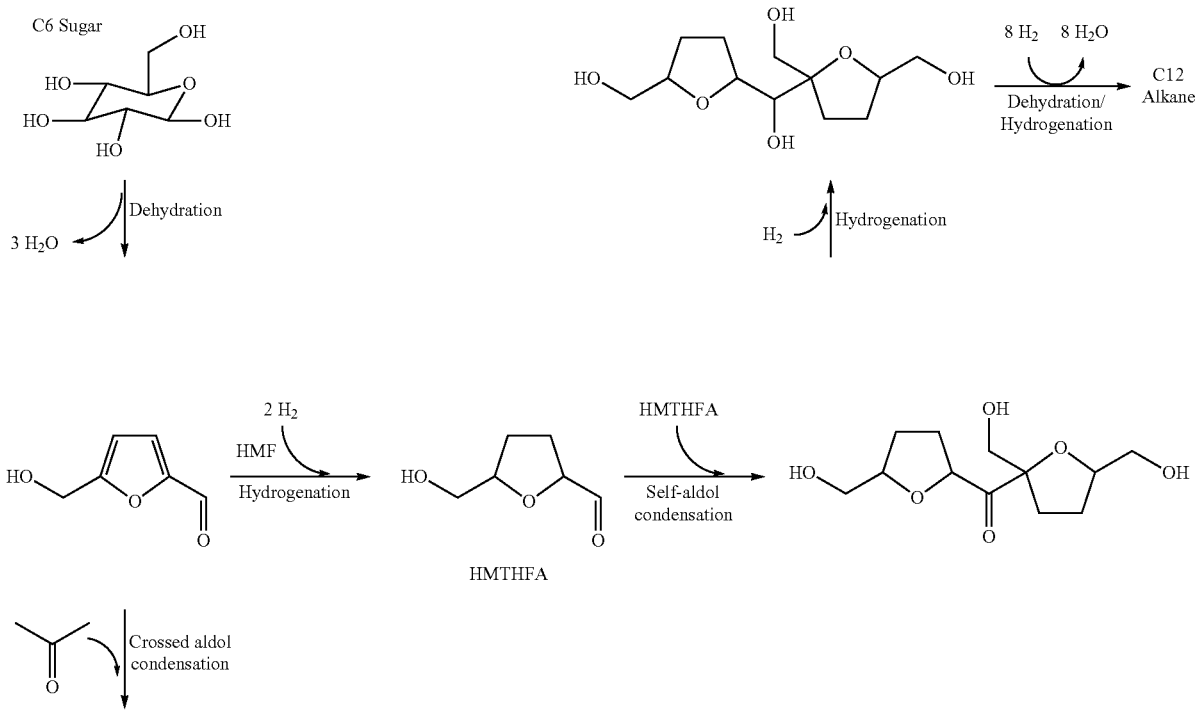

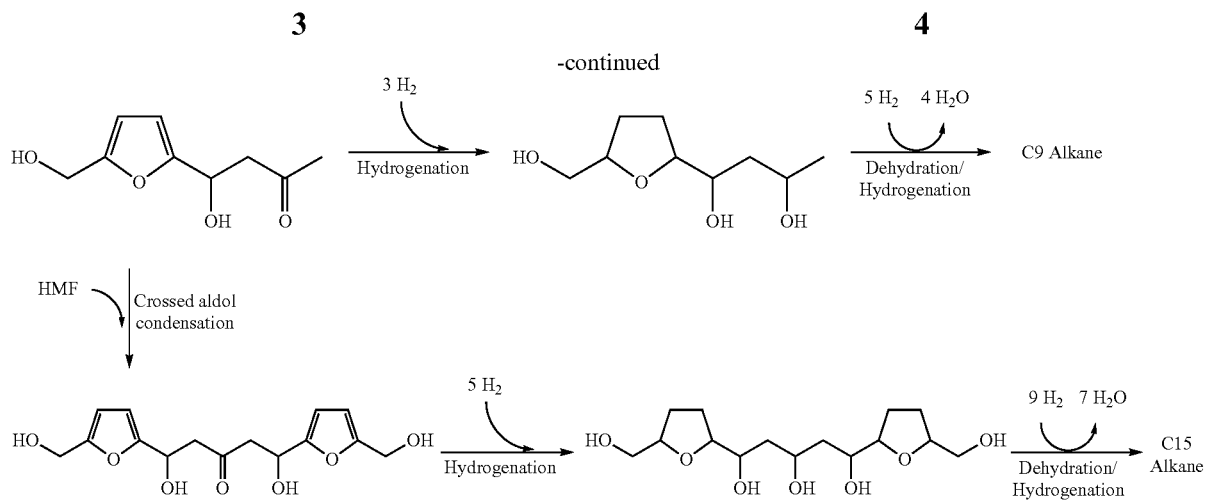

This has as a consequence that if we use stoichiometric ratios, which means 2 moles of furfural and 1 mol of acetone (since the acetone can react at both ends), between 16 and 37% of components with only 5 carbon atoms would be obtained that have a very limited interest as components for gasoline (*App. Catal. B Environ.* 2006, 66, 111-118). A second product with 8 carbon atoms which is usually one third of the mix appears in other conditions. This condensation product is hydrogenated to n-octane that does not have an interesting application in gasoline for having linear chain, or in diesel for the low molecular weight. To increase the selectivity to 85% with a yield of 71% the condensation has to be carried out in an aqueous phase, and the hydrogenation in hexadecane as a solvent at 120° C. which is a more expensive method (*Appl. Catal. B Environ.* 2006, 66, 111-118). The own authors realized the drawbacks caused by the selectivity and proposed as an alternative the hydrogenation of the furane ring to tetrahydrofurane since these derivatives are able to carry out an aldol condensation with themselves which would ensure a high selectivity. However, chemoselective hydrogenation of, e.g., furfural to tetrahydrofurfural in one step is still a challenge and is currently carried out in several stages. In any case, if a multi-stage method is accepted, molecules with a total of 10 carbon atoms can be obtained (*Science* 2005, 308, 1446-1450) the same as by furoin formation.

An alternative solution for the production of second-generation biofuels is described in R. D. Cortright, WO2008109877, 2007; *Int. Sugar J.* 2008, 110, 672-679 (FIG. 1), producing in a first step mixtures of compounds with 4 carbon atoms or more from oxygenated compounds in aqueous solution in the presence of a deoxygenation catalyst and a condensation catalyst (Aqueous Phase Reforming). With the purpose of obtaining high levels of alkanes the inventors use basic catalysts to condense ketones and aldehydes as in the case of Dumesic or the oligomerization of alkenes. However the way in which they combine molecules with low number of carbons is not sufficient to give molecules with a number of carbon atoms sufficiently high to be used as Diesel. Thus, the content in the raw products of molecules with ten carbon atoms or more is by below 50%. FIG. 1 illustrates the Cortright method.

Another interesting contribution of Dumesic (*Science* 2010, 327, 1110-1114) proposes the conversion of gamma-valerolactone in butene, water and carbon dioxide in a first step. In a second step the butene is oligomerized. The substrate used, gamma-valerolactone, had recently been identified as platform molecule that can be obtained by hydrogenation of levulinic acid, which is in turn platform molecule produced from agricultural waste. With his new method Dumesic manages to convert lactone in a mixture of alkenes of eight or more carbon atoms with a yield higher than 75%. However, the molecules with only eight carbon atoms are not suitable for the diesel fraction and due to this the diesel yield is reduced in twenty percent.

In other attempts to convert biomass into fuels, oxygenated products are obtained. These do not meet the requirement for the second-generation biofuels so that they can be used in the engines currently in use and they could, perhaps, be used as additives that can only be added to fuel in limited concentrations. Examples of these can be 2,5-dimethylfuran (*Nature*, 2007, 447, 982-986), or ethers or esters of 5-hydroxymethyl-furfural (PCT Int. Appl. WO2009030510, 2007).

Dumesic (*Angew. Chem. Int. Ed.* 2007, 46, 7164-7183), in addition to the methods explained above, describes other methods such as the dehydration and hydrogenation of sorbitol or xylitol to light linear alkanes. However, this last method cannot be considered as an alternative for producing hydrocarbons that increases the number of carbon atoms to more than the initial five or six (see also *Angew. Chem. Int. Ed.* 2004, 43, 1549-1551).

The present invention provides a method for transforming products derived from biomass into good quality diesel.

DESCRIPTION OF THE INVENTION

The present invention is related to a method for producing fuel having a high alkane content and a low oxygenized compounds content comprising at least:
  a first step of treating 2-methylfuran (commonly called Sylvan) with a catalyst and water in reaction conditions in order to form a mixture of products with at least ten carbon atoms, preferably with at least 15 carbon atoms.
  a second step of catalytic hydrogenation and dehydration of the mixture of products obtained in the first step, using preferably suitable hydrogenation and dehydration catalysts.

According to the present invention, in the first step molecules with at least 10 carbon atoms, preferably with 15 or more carbon atoms are built, which may be connected with at least other two carbon atoms with the exception of those constituting the end of the molecule, which are methyl groups. This mixture obtained in the first step is preferably a mixture of oxygenated hydrocarbons. A raw material that comes from monomers of carbohydrates is the starting material for building these molecules, which means from biomass. The great advantage of this type of built molecules is that they can be hydrogenated and dehydrated in one step to alkanes, to branched alkanes or to cyclic alkanes. Due to the number of carbon atoms that these products contain (hydrogenated and dehydrated) their boiling point is in the range of the boiling points of diesel.

It should be noted that if one tries to convert furfural or furfuryl alcohol under acid conditions you cannot obtain a usable product for fuels since both molecules in reaction conditions tend to polymerize forming products with high molecular weight (see e.g. *Makromol. Chem., Rapid Commun.* 1992, 13, 517-523). To avoid these polymerizations using biomass under alkylation/hydroalkylation conditions, in the present invention 2-methylfuran is used.

The starting compound 2-methylfuran or "Sylvan" can be obtained, for example, as a by-product in the production of furfuryl alcohol by hydrogenating furfural in vapor phase at 135° C. using a copper chromite catalyst (K. J. Zeitsch, The chemistry and technology of furfural and its many by-products, Elsevier, Amsterdam, 2000, p. 229). 2-methylfuran can also be obtained with the same catalyst increasing the temperature of reaction to 250° C. and increasing the hydrogen to furfural ratio to 6:1. In these conditions a 2-methylfuran yield of up to 92.5% can be obtained (L. E. Schniepp, H. H. Geller, R. W. von Korff, *J. Am. Chem. Soc.* 1947, 69, 672-674).

This direct synthesis of 2-methylfuran from pentose (or furfural) converts this molecule into a raw material suitable for the production of second generation biofuels such and as described in the present invention.

In the first step of the present invention 2-methylfuran is mixed with a catalyst and water resulting in a mixture of products with at least 10 carbon atoms, preferably at least 15 carbon atoms. Preferably, this mixture is a mixture of oxygenated hydrocarbons. According to a particular embodiment, the mixture of products obtained includes, at least, one oligomer of 2-methylfuran. Preferably, this oligomer is present in the mixture in at least 20% by weight.

The second step of the method of the present invention is a hydrogenation/dehydration of the mixture obtained after the treatment of 2-methylfuran (step 1) to give hydrocarbons that may contain one or several branches.

According to another particular embodiment of the present invention, the oligomer obtained in step 1 is a trimer of the 2-methylfuran.

According to a particular embodiment of the present invention, the oligomer obtained in the first step can be converted, under the reaction conditions, into other products that are suitable to be used in the second step. Preferably these products can be formed, for example, by the addition of water or by arylation with one or more molecules of 2-methylfuran or by a combination of both.

According to a preferred embodiment, the treatment of step 1 is carried out in the presence of an acid catalyst.

Moreover, preferably the treatment of step 1 is carried out in the presence of a mineral acid and more preferably in the presence of sulfuric acid. It is important to note that the use of sulfuric acid as a catalyst brings a great economic advantage since it is a very accessible and cheap acid.

According to another preferred embodiment of the present invention the treatment of step 1 is carried out in the presence of an insoluble acid in the medium. According to another particular embodiment of the present invention the treatment of step 1 is carried out in the presence of an acid resin, for example with sulfonic groups.

According to a preferred embodiment, the treatment of step 1 is carried out at a temperature between 0° C. and 200° C., more preferably between 0° C. and 100° C., while the hydrogenation/dehydration of step 2 is carried out preferably at a temperature between 180° C. and 450° C., more preferably between 220° C. and 400° C.

Moreover, preferably the hydrogenation of step 2 is carried out at a hydrogen pressure between 0.1 bars and 60 bars, preferably between 3 bars and 50 bars.

In the present invention, the hydrogenation catalyst used in step 2 may contain preferably a metal function and a dehydrating function. Preferably the catalyst of the second step comprises at least one of the elements selected from Re, Pd, Ru, Pt, Rh, Ni, or Cu which are preferably supported on a support selected from active carbon and inorganic oxides. According to a particular embodiment, the inorganic oxides have Lewis and/or Brönsted acidity and are preferably selected from alumina, zirconia, titania, silica, and combinations thereof.

The main advantages of the method according to the present invention are: the accessibility of the raw material at industrial large scale by hydrogenation of furfural, the high selectivity of the oligomerization method of 2-methylfuran (Sylvan) in the first step, the high selectivity of the hydrodeoxygenation method in the second step and the chemical and energy efficiency of the global method. It is important to note that it is not necessary any additional step of purification of the mixture of products obtained in the first step, thus avoiding additional energy expenditure consequently saving money and time. Globally, cellulosic biomass is transformed into a diesel in which the majority product is, preferably, a mixture of hydrocarbons with enough carbon atoms so that it can be added to the diesel currently marketed at service stations.

Another additional advantage of the present method from the ecological and economic viewpoint is that it does not need any solvent for its implementation. Moreover, the only byproduct formed in the hydrogenation/dehydration is water.

Throughout the description and the claims the word "comprises" and its variants are not intended to exclude other technical features, additives, components or steps. For the persons skilled in the art, other objects, features and advantages of the invention will emerge in part from the description and in part from the practice of the invention. The following examples are provided by way of illustration, and are not intended to be limiting of the present invention.

EXAMPLES

Next, non-limitative examples of the present invention will be described.

Example 1

Preparation of a Catalyst A for Hydrogenation/Dehydration

Norit 0.425 to 0.850 mm carbon active particles are impregnated with a solution of platinum hexachloride acid hexahydrate in deionized water at pore volume for obtaining a catalyst with a platinum concentration of three percent by weight. The material is dried at 60° C. for 12 hrs in an oven.

Example 2

Reactor for a Hydrogenation/Dehydration Reaction

In a stainless steel tube with an internal diameter of 1.11 cm and 18 cm in length are placed in the following order: 1.0 g of silicon carbide, as a catalyst bed 6.50 g of catalyst A and then 1.0 g of silicon carbide.

Example 3

Synthesis of a trimer of 2-methylfuran ($C_{15}H_{18}O_3$)

In a one liter three mouth flask, equipped with mechanical shaker and refrigerant, a mixture of 328 g of 2-methylfuran, 78.7 g of sulfuric acid (98%) and 249 g of water was stirred and heated at 60° C. for 16 hours.

The phases were separated, the organic phase was distilled under vacuum (140° C./2.9 Torr) and a compound with a mass of 246 was obtained, which coincides with the formula of $C_{15}H_{18}O_3$, with a yield of 76%.

$^{13}C$ RMN (75 MHz, $CDCl_3$) δ=208.3, 153.2, 151.0, 106.7, 106.0, 41.3, 38.1, 30.0, 26.9, 13.6.

Example 4

Synthesis of a Mixture of Products

In a one liter three mouth flask, equipped with mechanical shaker and refrigerant, a mixture of 328 g of 2-methylfuran, 78.7 g of sulfuric acid (98%) and 249 g of water was stirred and heated at 60° C. for 16 hours. The phases were separated, the organic phase was filtered and 93% by weight of the organic phase was obtained.

Example 5

Hydrogenation/dehydration of a trimer of 2-methylfuran ($C_{15}H_{18}O_3$)

238 g of the organic compound prepared in example 3 were passed through the reactor prepared in example 2 at a hydrogen pressure of 50 bar and at a temperature of reaction of 350° C. with a rate of 0.15 mL/min. 93% by weight of a liquid product that consisted of aqueous phase (19.3% by weight) and organic phase (81.7% by weight) was obtained. The organic phase was analyzed by two-dimensional gas chromatography (Agilent 7890A equipped with flow modulator and two columns, first column HP-5, 30 m, 0.25 mm inner diameter, 0.5 μm of film; second column Innowax, 5 m, 0.25 mm inner diameter, 0.15 μm of film; accumulation time of the modulator 1.0 sec, purge time of the accumulation tube of the modulator 0.12 sec, flow of hydrogen in the first column 1.26 mL/min, in the second column 24 mL/min). The chromatogram obtained was treated with the GC image software from the American company Zoex corporation and 90% of hydrocarbons with a number of carbon atoms between nine and fifteen, which can serve as diesel, was detected.

Example 6

Hydrogenation/Dehydration of a Mixture of Products 146 g of the organic phase prepared in example 4 were passed through the reactor prepared in example 2 at a hydrogen pressure of 50 bar and at a temperature of reaction of 350° C. with a rate of 0.12 mL/min. 92% by weight of a liquid product that consisted of aqueous phase (21% by weight) and organic phase (79% by weight) was obtained. The organic phase was analyzed by two-dimensional gas chromatography (conditions as described in example 5). The chromatogram obtained was treated with the GC image software from the American company Zoex corporation and 88% of hydrocarbons with a number of carbon atoms of nine or more, which can serve as diesel, was detected.

The invention claimed is:

1. A method for producing fuel comprising:
   a) contacting 2-methylfuran with a catalyst and water under suitable reaction conditions to form a mixture of products comprising at least one oligomer of 2-methylfuran having at least ten carbon atoms, and
   b) catalytically hydrodeoxygenating said mixture of products to produce the fuel.

2. The method according to claim 1, wherein the mixture of products is a mixture of oxygenated hydrocarbons.

3. The method according to claim 1, wherein the at least one oligomer is present in an amount of at least 20% by weight.

4. The method according to claim 1, wherein the mixture of products have at least 15 carbon atoms.

5. The method according to claim 1, wherein the catalyst of step a) is an acid catalyst.

6. The method according to claim 5, wherein the acid catalyst comprises a mineral acid.

7. The method according to claim 6, wherein the mineral acid comprises sulfuric acid.

8. The method according to claim 5, wherein step a) is carried out in the presence of an insoluble acid.

9. The method according to claim 5, wherein step a) is carried out in the presence of an acid resin.

10. The method according to claim 1, wherein the reaction of step a) is carried out at a temperature between 0° C. and 200° C.

11. The method according to claim 1, wherein the hydrodeoxygenation is carried out at a temperature between 180° C. and 450° C.

12. The method according to claim 1, wherein the hydrodeoxygenation is carried out at a hydrogen pressure between 0.1 bar and 60 bar.

13. The method according to claim 1, wherein the hydrodeoxygenation catalyst comprises at least a metal function and a dehydrating function.

14. The method according to claim 13, wherein the hydrodeoxygenation catalyst comprises at least one of the elements selected from Re, Pd, Ru, Pt, Rh, Ni, and Cu, and further comprises a support.

15. The method according to claim 14, wherein the support is selected from active carbon, an inorganic oxide and combinations thereof.

16. The method according to claim 15, wherein the support is an inorganic oxide selected from alumina, zirconia, titania, silica and combinations thereof.

17. The method according to claim 10, wherein the reaction of step a) is carried out at a temperature between 0° C. and 100° C.

18. The method according to claim 11, wherein the hydrodeoxygenation is carried out at a temperature between 220° C. and 400° C.

19. The method according to claim 12, wherein the hydrodeoxygenation is carried out at a hydrogen pressure between 3 bar and 50 bar.

* * * * *